United States Patent [19]

Friese et al.

[11] Patent Number: 5,686,654
[45] Date of Patent: Nov. 11, 1997

[54] MEASURING SENSOR FOR DETERMINING THE OXYGEN CONTENT IN GAS MIXTURES

[75] Inventors: Karl-Hermann Friese, Leonberg; Werner Gruenwald, Gerlingen, both of Germany

[73] Assignee: Robert Bosch GmbH, Stuttgart, Germany

[21] Appl. No.: 687,600

[22] PCT Filed: Nov. 28, 1995

[86] PCT No.: PCT/DE95/01685

§ 371 Date: Aug. 8, 1996

§ 102(e) Date: Aug. 8, 1996

[87] PCT Pub. No.: WO96/20400

PCT Pub. Date: Jul. 4, 1996

[30] Foreign Application Priority Data

Dec. 28, 1994 [DE] Germany ............... 44 47 033.9

[51] Int. Cl.⁶ .................. G01N 27/416; G01N 27/419
[52] U.S. Cl. ............... 73/23.32; 73/23.31; 73/31.05; 73/116; 60/276
[58] Field of Search ................ 73/23.31, 23.32, 73/31.05, 31.06, 116, 117.2, 117.3, 118.1; 60/276, 277; 364/431.062

[56] References Cited

U.S. PATENT DOCUMENTS

| | | | |
|---|---|---|---|
| 4,440,621 | 4/1984 | Kitahara et al. | 204/406 |
| 4,753,203 | 6/1988 | Yamada et al. | 123/440 |
| 4,909,072 | 3/1990 | Logothetis et al. | 73/116 |
| 5,089,113 | 2/1992 | Logothetis et al. | 204/425 |
| 5,236,569 | 8/1993 | Takao et al. | 204/412 |
| 5,476,001 | 12/1995 | Hoetzel et al. | 73/118.1 |

FOREIGN PATENT DOCUMENTS

| | | |
|---|---|---|
| 3632456 | 4/1987 | Germany. |
| 4311849 | 10/1994 | Germany. |
| 2285866 | 7/1995 | United Kingdom. |

*Primary Examiner*—George M. Dombroske
*Attorney, Agent, or Firm*—Spencer & Frank

[57] ABSTRACT

A measuring sensor for determining the oxygen content in gas mixtures including exhaust gases of internal combustion engines, includes a first electrochemical pump cell and a second electrochemical pump cell; an internal reference gas source; a measuring gas chamber which is connected to the gas mixture; electrodes for the first and the second pump cell; a first pumping voltage ($U_{P1}$) for the first pump cell and a second pumping voltage ($U_{P2}$) for the second pump cell; wherein oxygen is pumped into the internal reference gas source by means of the first pumping voltage, wherein a pumping current is driven by the second pumping voltage and is measured as a measure for the partial oxygen pressure, wherein the first pumping voltage ($U_{P1}$) and the second pumping voltage ($U_{P2}$) are set such that more oxygen is pumped into the reference gas source by way of the first pumping voltage ($U_{P1}$) than is pumped out of the reference gas source by the second pumping voltage ($U_{P2}$), and wherein the first pump cell is acted upon by a first operating voltage ($U_{B1}$) and the second pump cell is acted upon by a second operating voltage ($U_{B2}$) so that, under the action of the corresponding Nernst voltages, the first pumping voltage ($U_{P1}$) is always larger than the second pumping voltage ($U_{P2}$) at a polarity which is reversed compared to the first pumping voltage ($U_{P1}$).

6 Claims, 1 Drawing Sheet

MEASURING SENSOR FOR DETERMINING THE OXYGEN CONTENT IN GAS MIXTURES

BACKGROUND OF THE INVENTION

1. Field of the Invention

The invention relates to a measuring sensor for determining the oxygen content in gas mixtures, particularly in exhaust gases of internal combustion engines, of the generic type of the main claim, namely, one having a first electrochemical pump cell and a second electrochemical pump cell, having an internal reference gas source and a measuring gas chamber which is connected to the gas mixture, having electrodes for the first and the second pump cell, and having a first pumping voltage for the first pump cell and a second pumping voltage for the second pump cell, with oxygen being pumped into the reference gas source by means of the first pumping voltage and the second pumping voltage driving a pumping current, which is measured as a measure for the partial oxygen pressure. A measuring sensor of the generic type is known from DE 36 32 456 C2, wherein, instead of atmospheric air as comparison gas or reference gas, oxygen is pumped from the gas mixture to be measured into an internal reference gas source. For this purpose, a first pump cell and a second pump cell, each having two electrodes, and a gas chamber are provided, with respectively one electrode of the first and second pump cell being arranged in the gas chamber and the gas chamber being connected with the gas mixture via a diffusion barrier. The second electrode of the first pump cell is connected with the internal reference gas source. The second electrode of the second pump cell is exposed to the gas mixture. With the first pump cell, oxygen is constantly pumped under the action of a pumping current from the measuring gas chamber into the internal reference gas source. The second pump cell is operated by means of a bidirectional control such that an approximately constant partial oxygen pressure is generated in the measuring gas chamber by pumping oxygen in or out. The pumping voltage of the second pump cell is compared to a constant reference voltage. The pumping current is controlled bidirectionally by way of the voltage difference. The pumping current itself serves as measure for the oxygen content in the gas mixture.

SUMMARY OF THE INVENTION

The measuring sensor having the characterizing features of the main claim, namely, characterized in that the first pumping voltage ($U_{P1}$) and the second pumping voltage ($U_{P2}$) are set such that by way of the first pumping voltage ($U_{P1}$) more oxygen is pumped into the reference gas source than is pumped out of the reference gas source by second pumping voltage ($U_{P2}$), which has the advantage that it can operate without a bidirectional control of the pumping current, which means that the evaluation electronics can be simplified.

Advantageous modifications of the sensor according to the invention are possible by means of the measures listed in the dependent claims. The first pump cell may be acted upon by a first operating voltage ($U_{B1}$) and the second pump cell may be acted upon by a second operating voltage ($U_{B2}$) so that, under the action of the corresponding Nernst voltages, the first pumping voltage ($U_{P1}$) is always larger than the second pumping voltage ($U_{P2}$) at a polarity which is reversed compared to the first pumping voltage ($U_{P1}$).

The operating voltage ($U_{B1}$) of the first pump cell (10) may be dimensioned according to the condition $U_{B1} > 2U_{Nf}$, $U_{B2}$, with $U_{Nf}$=Nernst voltage is the rich gas mixture. The second operating voltage ($U_{B2}$) advantageously has the value of the Nernst voltage at $\lambda=1$, preferably 450 mV.

An electrode of the first pump cell and an electrode of the second pump cell may be arranged in the reference gas source. The electrode of the first pump cell and of the second pump cell may be arranged in the reference gas source and may be joined to form one electrode. The one electrode of the second pump cell may be arranged in the measuring gas chamber and the measuring gas chamber may be connected to the gas mixture via a diffusion barrier. The reference gas source may be provided with a pressure compensation connection which leads to the gas mixture and/or to the atmospheric air. The reference gas source may be formed by a porous heating element insulation. It is particularly advantageous to set the operating voltage of the second pump cell such that at $\lambda=1$ the resulting pumping voltage of the second pump cell becomes zero. Therewith it is possible to prevent the total voltage between the electrodes of the first and second pump cell from rising beyond a value which results in electrolyte decomposition. A reduction of the number of terminals for the measuring sensor is accomplished if the electrodes of the first pump cell and of the second pump cell, which electrodes are arranged in the reference gas source, are joined to form a common electrode. Furthermore, it is particularly advantageous to place the reference gas source into a porous heating element insulation and to create a pressure compensation connection to the atmospheric air.

BRIEF DESCRIPTION OF THE DRAWINGS

Two embodiments of the invention are illustrated in the drawings and explained in greater detail in the description below.

DESCRIPTION OF THE PREFERRED EMBODIMENTS

Figure 1:
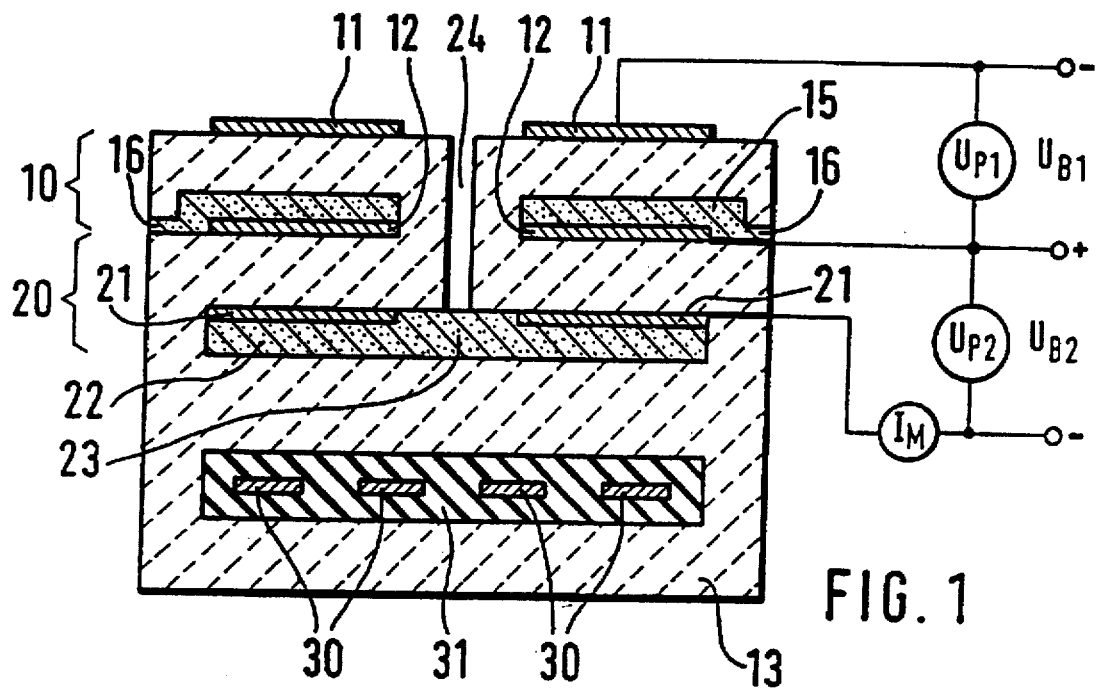
FIG. 1 shows a cross section of a first embodiment of a measuring sensor according to the invention and FIG. 2 a cross section of a second embodiment of a measuring sensor according to the invention.

The measuring sensor according to FIG. 1 is provided with a reference cell 10 having a first electrode 11 and a second electrode 12, with a measuring cell 20 having a third electrode 21 and with a resistance heating element 30. The electrodes 11, 12, 21 are connected to an oxygen-ion-conducting solid electrolyte body 13. The electrodes 11, 12, 21 are comprised, for example, of platinum or platinum cermet. The resistance heating element 30 is embedded into the solid electrolyte body 13 by means of an electrical insulation 31 and is comprised, for example, of the same material as the electrodes. The first electrode 11 is arranged on the outside of the solid electrolyte body 13 and exposed directly to the gas mixture, with the option that a porous protective layer, not shown, is additionally placed over the electrode 11.

The solid electrolyte body 13 is comprised of several solid electrolyte films, not illustrated in detail, in-between which the electrodes 11, 12, 21, the insulation 31 and the resistance heating element 30 are arranged as layers. The solid electrolyte films provided with the layers are laminated together and sintered. The fabrication of such a planar sensor element is generally known so that a more detailed description can be dispensed with in this context. As a material for the solid electrolyte body 13, zirconium oxide is particularly suitable which is stabilized by bivalent and/or trivalent oxides having a similar cation radius as that of the tetravalent Zr cation, for example, by CaO or $Y_2O_3$.

A measuring gas chamber 22 is disposed in the solid electrolyte body 13, in which chamber the third electrode 21 is arranged. The measuring gas chamber 22 is embodied with a diffusion barrier 23 which is formed, for example, by filling the measuring gas chamber 22 with a porous material, for example, with aluminum oxide. A diffusion channel 24 leads to the measuring gas chamber 22 so that the gas mixture to be measured can reach the measuring gas chamber 22 via the diffusion channel 24.

The solid electrolyte body 13 comprises a further gas chamber 15 having a pressure compensation connection 16 which leads, for example, to the gas mixture. The second electrode 12 is arranged in the gas chamber 15, via which electrode oxygen is pumped into the gas chamber 15 so that an internal reference gas source is formed in the gas chamber 15. To prevent excess pressure in gas chamber 15, a portion of the oxygen pumped into gas chamber 15 can escape into the gas mixture via the pressure compensation connection 16. Here, the pressure compensation connection 16 is advisably embodied such that a back diffusion of oxidizable gas constituents into the gas chamber 15 is avoided.

In the place of electrode 12, it is also possible, however, that two individual electrodes are arranged in the gas chamber 15, with one electrode then being allocated to the reference cell 10 and the other electrode to the measuring cell 20. The gas chamber 15 is produced, for example, by a porous aluminum oxide layer. Furthermore, it is conceivable to utilize the pores of porous electrodes as gas chamber 15.

The reference cell 10 and the measuring cell 20 are operated as pump cells. The electrodes 11 and 12 of the reference cell 10 are acted upon by a first operating voltage $U_{B1}$ and the electrodes 12 and 21 of the measuring cell 20 by a second operating voltage $U_{B2}$. A Nernst voltage counteracts the operating voltages $U_{B1}$ and $U_{B2}$; the Nernst voltage amounts to approx. 900 mV at $\lambda<1$, approx. 450 mV at $\lambda=1$ and approx. 30 mV at $\lambda>1$. The operating voltage $U_{B1}$ is polarized such that electrode 11 acts as cathode and electrode 12 as anode, because of which oxygen is pumped from electrode 11 to electrode 12. The operating voltage $U_{B2}$ has a polarity such that in the lean gas mixture, electrode 21 acts as cathode and electrode 12 as anode, and in the rich gas mixture, electrode 12 acts as cathode and electrode 21 as anode. This means that the polarity of the electrodes is reversed when the mixture changes from lean to rich. This is accomplished in that the operating voltage $U_{B2}$ is set to the value of the Nernst voltage at $\lambda=1$ of approximately 450 mV.

A prerequisite for the operation of the measuring sensor is that the partial oxygen pressure in gas chamber 15 is always higher than in the gas mixture. For this purpose, the operating voltage $U_{B1}$ is set to a value which ensures that more oxygen is always pumped into gas chamber 15 by reference cell 10 than can be pumped out of gas chamber 15 by the measuring cell 20 when the polarity in the rich gas mixture is reversed. This value is reached by the following condition:

$$U_{B1} > 2U_{Nf} - U_{B2}$$

with $U_{Nf}$=Nernst voltage in the rich gas mixture.

In the present embodiment, the operating voltage $U_{B2}$ is set to 450 mV. Accordingly, the operating voltage $U_{B1}$ must be at least 1350 mV (2×900 mV−450 mVM=1350 mV). In the present embodiment, the operating voltage $U_{b1}$ is 1.6 V.

The operating voltage $U_{B1}$ generates a first pumping voltage $U_{P1}$, by which a constant pumping current $I_P$ is driven by, for example, 50 μA. By means of the pumping current $I_P$, oxygen is continuously pumped from electrode 11 to electrode 12 into gas chamber 15.

The measuring sensor works as follows: The partial oxygen pressure of the gas mixture to be measured occurs at electrode 11 of reference cell 10 and via the diffusion barrier 23 at electrode 21 of measuring cell 20. In a lean gas mixture ($\lambda>1$), the oxygen is reduced cathodically because of the active pumping voltage $U_{P1}$ at electrode 11 and is pumped in ion form to electrode 12 and is discharged there as oxygen. This means that a higher partial oxygen pressure is generated in gas chamber 15 than in the gas mixture. The Nernst voltage of approximately 30 mV created during this process counteracts the operating voltage $U_{B1}$ of 1.6 V so that the resulting pumping voltage $U_{P1}$ of 1570 mV is only slightly smaller than the operating voltage $U_{B1}$. The same Nernst voltage of 30 mV also counteracts the second operating voltage $U_{B2}$. With 420 mV, the pumping voltage $U_{P2}$ also pumps oxygen from the measuring chamber 22 to the gas chamber 15. This causes a cathodic limiting current $I_M$ to flow which is used as a measure for the partial oxygen pressure in the gas mixture.

If the partial oxygen pressure in the exhaust gas approaches the stoichiometric fuel-air ratio ($\lambda=1$), a Nernst voltage of approximately 450 mV, which corresponds to this partial pressure, is superposed over the first operating voltage $U_{B1}$ and the second operating voltage $U_{B2}$. This reduces the pumping voltage $U_{P1}$ to a value of approximately 1150 mV. The pumping voltage $U_{P2}$ becomes zero. This means that $\lambda=1$, a pumping current $I_M$ does not flow.

If the gas mixture changes to the rich range ($\lambda<1$), the first operating voltage $U_{B1}$ and the second operating voltage $U_{B2}$ are superposed by a Nernst voltage of approximately 900 mV which corresponds to the partial oxygen pressure at $\lambda<1$. The first pumping voltage $U_{P1}$ is reduced to 700 mV. The second operating voltage $U_{B2}$ of 450 mV is also superposed by the 900 mV Nernst voltage so that the polarity of the pumping voltage $U_{P2}$ is reversed. Thus, electrode 12 becomes the cathode and electrode 21 the anode. In this manner, the oxygen at electrode 12 is reduced cathodically and pumped to electrode 21 in ion form and is discharged in measuring gas chamber 22. The pumping voltage $U_{P2}$ of 450 mV resulting from the voltage difference thus drives an anodic limiting current $I_M$. The limiting current $I_M$ flows in the opposite direction. The amount of the anodic limiting current $I_M$ indicates the partial oxygen pressure in the gas mixture. Since at $\lambda<1$ the pumping voltage $U_{P1}$ is also larger than the oppositely acting pumping voltage $U_{P2}$, reference cell 10 pumps more oxygen into gas chamber 15 than the measuring cell 20 pumps out of gas chamber 15. As a result, the partial oxygen pressure in the gas chamber 15 continues to be larger than in the gas mixture.

With an evaluation circuit, not shown, the current direction and the amount of the limiting current $I_M$ are captured and supplied to an electronic control system, not shown, by means of which the fuel-air ratio of the fuel mixture is adjusted. Thus, the measuring sensor can be used to determine the oxygen content for lean, neutral and rich gas mixtures.

Figure 2:
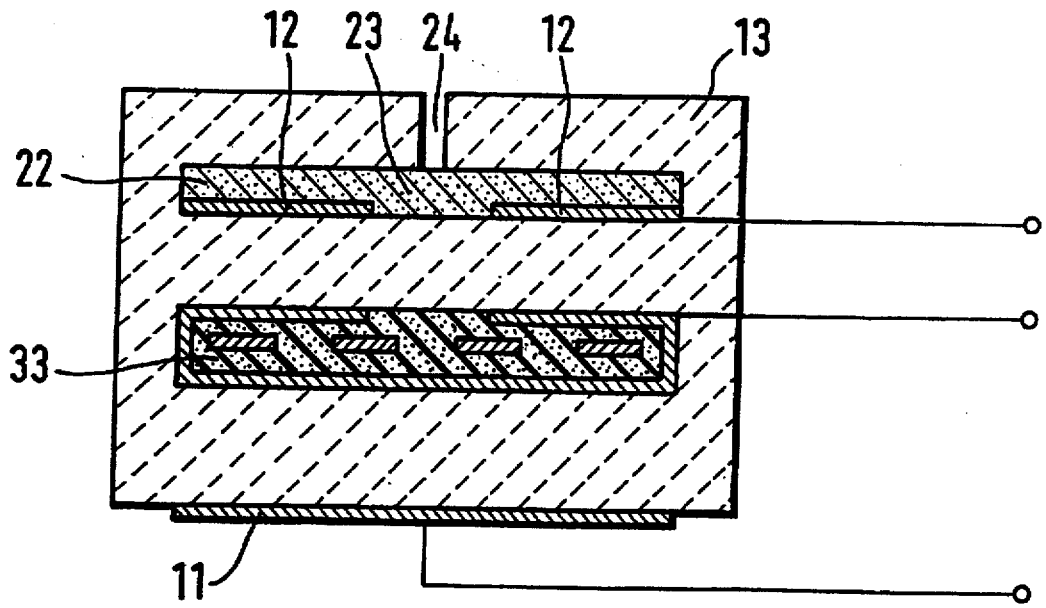

A second embodiment of the invention is illustrated in FIG. 2; in this embodiment, a porous heating element insulation 33 for the resistance heating element 30 is integrated into the solid electrolyte body 13. The second electrode 12 of reference cell 10 is disposed in the heating element insulation 33. The porous heating element insulation 33 thus forms gas chamber 15. In this embodiment, it is advisable to embody the surface of electrode 12 in the heating element insulation 33 to be so large that it faces electrode 11, which is arranged on the outside surface, as well as electrode 21, which is disposed in the measuring gas chamber 22. The pressure compensation connection for the gas chamber 15 is not shown in FIG. 2. But it is disposed on the terminal-side end of the measuring sensor so that the gas chamber 15 with the reference gas source does not lead into the gas mixture but to the atmospheric air. This prevents possible back diffusions of gas constituents from the gas mixture into the gas chamber 15. The operation of the measuring sensor according to FIG. 2 takes place analogously to that of the measuring sensor according to FIG. 1.

What is claimed is:

1. A measuring sensor for determining the oxygen content in gas mixtures including exhaust gases of internal combustion engines, the measuring sensor comprising:

a first electrochemical pump cell and a second electrochemical pump cell;

an internal reference gas source;

a measuring gas chamber which is connected to the gas mixture;

electrodes for the first and the second pump cell;

a first pumping voltage ($U_{P1}$) for the first pump cell and a second pumping voltage ($U_{P2}$) for the second pump cell;

wherein oxygen is pumped into the internal reference gas source by means of the first pumping voltage, wherein a pumping current is driven by the second pumping voltage and is measured as a measure for the partial oxygen pressure, wherein the first pumping voltage ($U_{P1}$) and the second pumping voltage ($U_{P2}$) are set such that more oxygen is pumped into the reference gas source by way of the first pumping voltage ($U_{P1}$) than is pumped out of the reference gas source by the second pumping voltage ($U_{P2}$), and wherein the first pump cell is acted upon by a first operating voltage ($U_{B1}$) and the second pump cell is acted upon by a second operating voltage ($U_{B2}$) so that, under the action of the corresponding Nernst-voltages, the first pumping voltage ($U_{P1}$) is always larger than the second pumping voltage ($U_{P2}$) at a polarity which is reversed compared to the first pumping voltage ($U_{P1}$).

2. The measuring sensor according to claim 1, wherein the first operating voltage ($U_{B1}$) of the first pump cell is dimensioned so that:

$$U_{B1} > 2U_{Nf} - U_{B2},$$

where $U_{Nf}$=Nernst voltage in a rich gas mixture.

3. The measuring sensor according to claim 2, wherein the second operating voltage ($U_{B2}$) has the value of the Nernst voltage at $\lambda=1$.

4. The measuring sensor according to claim 3, wherein the second operating voltage ($U_{B2}$) is 450 mV.

5. The measuring sensor according to claim 1, wherein the second operating voltage ($U_{B2}$) has the value of the Nernst voltage at $\lambda=1$.

6. The measuring sensor according to claim 5, wherein the second operating voltage ($U_{B2}$) is 450 mV.

* * * * *